United States Patent [19]

Hetzel et al.

[11] 4,076,577
[45] Feb. 28, 1978

[54] PROCESS FOR THE SEPARATION OF RESIDUES OF TOLUENEDIISOCYANATE PRODUCTION

[75] Inventors: Eckard Hetzel; Waldemar Koehler, both of Frankenthal; Georg Friedrich Vock, Ludwigshafen; Rolf Bittler, Heidelberg, all of Germany

[73] Assignee: BASF Wyandotte Corporation, Wyandotte, Mich.

[21] Appl. No.: 628,358

[22] Filed: Nov. 3, 1975

[30] Foreign Application Priority Data

Nov. 7, 1974 Germany .............................. 2452805

[51] Int. Cl.² ............................................. B01D 1/00
[52] U.S. Cl. .............................. 159/47 R; 159/25 A; 202/175; 260/453 SP
[58] Field of Search ...................... 159/47, 25 A, 25 R; 260/453 AR, 453 AM, 453 PH, 453 SP; 202/175

[56] References Cited

U.S. PATENT DOCUMENTS

| 2,911,429 | 11/1959 | Bloom et al. ................... 260/453 PH |
| 3,287,387 | 11/1966 | Denton et al. ................... 260/453 PH |
| 3,508,882 | 4/1970 | Farnell ............................... 159/25 A |

FOREIGN PATENT DOCUMENTS 2,058,032    5/1972    Germany ..................... 260/453 PH

*Primary Examiner*—Norman Yudkoff
*Attorney, Agent, or Firm*—Robert J. Henry; Bernhard R. Swick; Robert E. Dunn

[57] ABSTRACT

A process for the separation of residues of toluenediisocyanate production from mixtures containing high boiling residues, toluenediisocyanate and solvent by evaporation in said residue at a minimum of 5° C above the boiling point of the higher boiling of the components consisting of toluenediisocyanate and solvent. The mixture is fed into the central portion of an evaporator equipped with a helical agitator operative to provide a material flow moving centrally downwards and peripherally upwards.

11 Claims, 1 Drawing Figure

U.S. Patent     Feb. 28, 1978     4,076,577
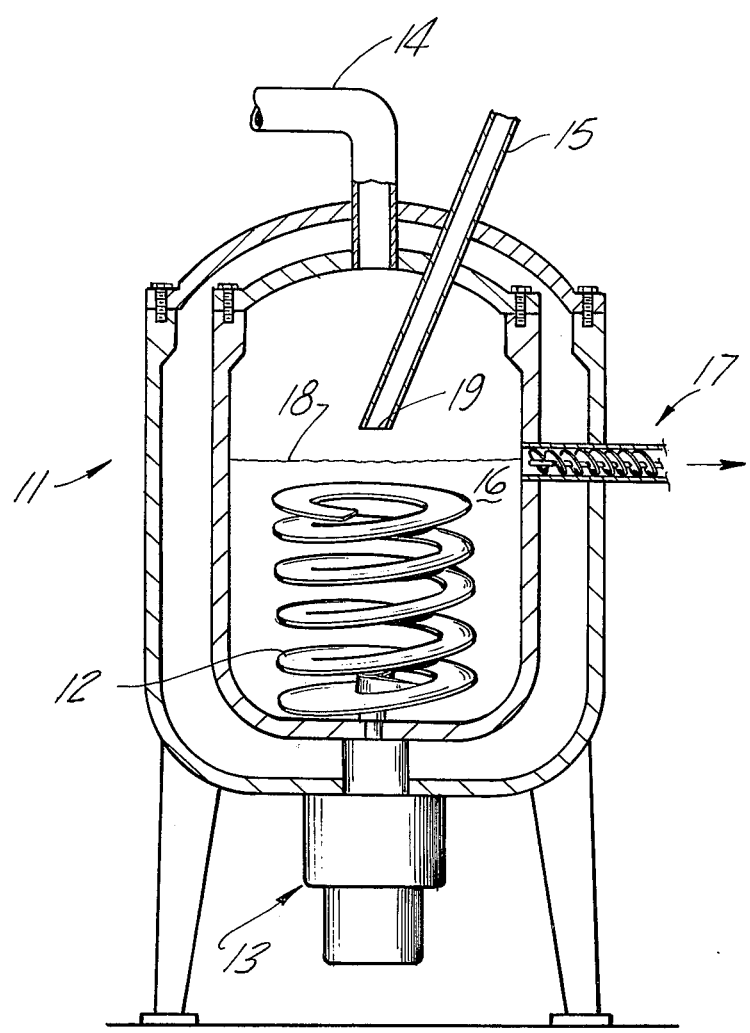

PROCESS FOR THE SEPARATION OF RESIDUES OF TOLUENEDIISOCYANATE PRODUCTION

BACKGROUND OF THE INVENTION

1. Field of the Invention

The present invention relates to a process for the separation of residues of toluenediisocyanate production, and more particularly to the separation of residues from mixtures obtained after reaction of toluenediamine and phosgene and preliminary separation thereof.

2. Description of the Prior Art

It is known from Ullmanns Encyklopadie der technischen Chemie [Ullmann's Encyclopedia of Industrial Chemistry] (1957), Vol. 9, pp. 8–10, that toluenediamine in the presence of an organic solvent having a boiling point lower than toluenediisocyanate, e.g., o-dichlorobenzene, is converted with phosgene into toluenediisocyanate. Generally, phosgenation is performed at low and high temperatures. As a rule, the reaction solution is then freed from residual phosgene by distillation or by entrainment with a stream of nitrogen and from the major amount of organic solvent by concentration in a distillation system. The reaction solution (concentrate) obtained usually contains 65–98 weight percent toluenediisocyanate, 0–10 weight percent lower-boiling organic solvent and 2–25 weight percent of nonvolatile residues. If higher-boiling organic solvents are used, for example, diethylisophthalate, it is advisable for the reaction and removal of residual phosgene to be followed by removal of toluenediisocyanate by distillation, resulting in a mixture (concentrate) of 70–98 weight percent of organic solvent, e.g., diethylisophthalate, 0–5 weight percent toluenediisocyanate and 2–25 weight percent of nonvolatile residues in the form of a solution or suspension.

The above-mentioned mixtures (concentrates) are now concentrated by distillation and the nonvolatile residues are thus separated from the fractions of the mixture of end-product and solvent, respectively, which are of interest in view of process economy, increase of end-product yield and reusable solvent. The last step consists of evaporation in customary evaporators, e.g., in residue pots in vacuum (Ullmann, loc. cit., top of p. 10).

Residues to be considered are urea derivatives, e.g., N,N'-di-(aminotoluyl) ureas, di-[(N-aminophenyl-)ureido-(N')] toluenes, N,N'-di-(isocyanatotoluyl) ureas, di-[(N-isocyanatophenyl)-ureido-(N')] toluenes and corresponding biurets; uretdiones, e.g., N,N'-di-(aminotoluyl)-1,3-diazacyclobutane-2,4-dione, N,N'-di-(isocyanatotoluyl)-1,3-diazacyclobutane-2,4-dione; isocyanuric acid esters, e.g., tri-(aminotoluyl) isocyanurates, tri-(isocyanatotoluyl) isocyanurates; carbodiimides, e.g., di-(aminotoluyl) carbodiimides, di-(isocyanatotoluyl) carbodiimides. Since the mentioned compounds still contain active groups, such as amino- or isocyanate-groups, they can condense again, particularly during heating and/or in the presence of, e.g., fractions of starting diamine or phosgene, so that the residues will also contain corresponding di-, tri- or polyureas, di-, tri-, polyuretdiones, di-, tri-, polyisocyanuric acid esters, di-, tri-, polycarbodiimides, and in particular, polymers which simultaneously contain several ureide groups, biuret groups, carbodiimide groups and/or isocyanurate groups in the molecule. The compounds may be chlorinated in the ring and side chain. Depending on the solvent utilized, reaction products of toluenediamine or the mentioned compounds with decomposition products of the solvent may form, for example, the amide of formula

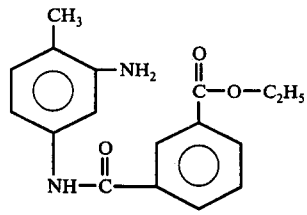

from toluenediamine and decomposition products of diethylisophthalate.

In addition, metal chlorides may be present in the residue from corrosion processes. Generally, depending on the synthesis conditions, the residues contain 1–80 weight percent urea compounds, 0–40 weight percent uretdiones, 0–60 weight percent isocyanuric acid esters, 0.5–20 weight percent carbodiimides, and 5–95 weight percent more highly condensated or polymeric materials.

If such residues are heated in one step in the presence of active groups, as is the case, for example, during evaporation of the mentioned concentrates, continuous changes take place in the form of decomposition, chain rupture, ring scission and, particularly, further condensations. Such residues furthermore pass through high-viscosity phases during evaporation. On contact with hot wall surfaces or agitating equipment, this leads to caking and build-up. Deposits on the heating surfaces impair heat transfer. Very long drying times become necessary and evaporation is incomplete, while losses of solvent or toluenediisocyanate occur.

It is known from German Pat. No. 1,218,265 that materials in powder form can be mixed with helical agitators. It describes that products in the form of powder and fine granulate often tend to fuse or sinter during mixing and are unfavorably modified by the frictional heat generated during mixing. Such difficulties occur particularly with polymers, such as polyethylene or polypropylene. The individual particles fuse and sinter, inhibit the mixing motion, deposit on the agitator and with time, form large fused polymer coagulates. In such mixing processes, the product is forced downward in the center of the vessel and forced upward again on the vessel walls, and during deflection the mixed product is under high compressive and shear stresses at the vessel bottom. Such stresses increase the mentioned difficulties. The patent states (column 1) that products which tend to cake cannot be mixed by this method and recommends a specially designed helical agitator as the agitating equipment by means of which the powder materials are not caused to fuse or sinter by the generated heat of friction.

SUMMARY OF THE INVENTION

It has now been found that residues formed during the reaction of toluenediamine and phosgene in the presence of organic solvents can be advantageously separated from a mixture of these residues with toluenediisocyanate or a solvent of higher boiling point than toluenediisocyanate by evaporating the mixture in an evaporator, if the mixture is fed from the head into the center of the evaporator and is evaporated at a temperature at least 5° C above the boiling point of toluenediisocyanate or the solvent having a boiling point higher than toluenediisocyanate, while the mixture is mixed with a helical agitator rotating at a speed of 2-100 rpm.

The reaction which has preceded the separation is represented by the following formulas for the case when 2,4-toluenediamine is used:

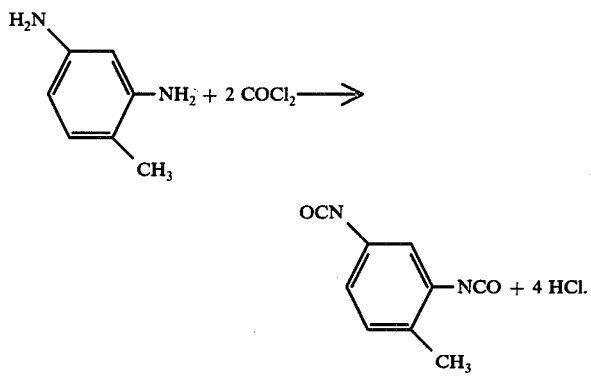

In view of the state of the art, the process of the invention provides a practically complete separation of the residues of toluenediisocyanate production and thus leads to toluenediisocyanate in better yield and purity and by a simpler and more economical method. Caking, build-up, viscosity increase of the residues and the evaporating mixture do not occur. Accordingly, thermal conduction and agitating efficiency are improved, evaporation is more rapid and complete at a relatively lower agitating energy. Long drying times are not needed and thus, operating personnel and control equipment are also saved. In particular, further modification of the residues during evaporation, e.g., decomposition, cleavage, recondensation, polymerization, and particularly, a further formation of residues by decomposition or conversion of toluenediisocyanate with the previously existing residues are avoided to a substantial degree. All of these favorable results are surprising, for in view of the process described in German Pat. No. 1,218,265, in which only dry materials in powder form are to be prevented from fusing and sintering, it should have been expected that solutions or suspensions which pass through high-viscosity phases, sintering phases and melting phases during evaporation, would surely give rise to the mentioned difficulties.

BRIEF DESCRIPTION OF THE DRAWING

In the accompanying drawing, in which like numerals are used to designate like parts throughout, the single figure illustrates a typical apparatus that may be used to carry out the process of the invention.

DETAILED DESCRIPTION OF THE PREFERRED EMBODIMENT

Referring now more particularly to the drawing, there is shown an evaporator 11 equipped with helical agitator 12, driven externally through the bottom with a suitable drive mechanism 13. The evaporator is jacketed to receive a suitable heating fluid for providing a controlled temperature therein. Exit duct 14 is provided for removing gases, and inlet 15 is provided for supplying feed material. As here shown, the evaporator is charged with residue 16, which is in a substantially dry solid state, and present to about the level of exit means 17. The exit means is formed to remove residue from near the periphery of the evaporator and maintain a surface 18 of material just below the discharge end 19 of feed inlet 15. Suitable controls which are well known in the art are not illustrated, but these controls provide for accurately maintaining the temperature and pressure within the evaporator.

In operation, the starting mixture is fed in at the feed site in the center of the vessel, is then conducted downward in a flow in the vertical central zone, gradually loses its fraction of volatiles, and finally, during deflection at the vessel bottom and in the flow from, the bottom to the top along the peripheral zone of the total mixture, converts into dry solid residues which are again moved in the cycle in the upper layer of the total mixture from outside to inside and thus toward the vertical center zone containing the volatile fractions of the starting mixture. Thus, during the continuous mixing process, all degrees of moisture of the residues are present and with the helical agitator described in the German patent and, even more so, with the helical agitators of conventional design, it was to be expected that this interaction of more or less wet residue particles would result in a considerable degree of caking and the above-mentioned difficulties.

The starting mixture consists of mixtures originating from the reaction of 2,3-, 2,5-, 3,4-, 3,5-, or particularly, 2,4- and 2,6-toluenediamine with phosgene in the presence of organic solvents having a lower or higher boiling point than the correspondingly produced toluenediisocyanate, preferably the concentrates of the above-described composition. A residue fraction in the starting mixture of 0.2-70, preferably 2-60 weight percent, is of advantage. The volatiles may be toluenediisocyanate and lower-boiling solvents, appropriately in a ratio of 0-10 weight percent of lower-boiling solvent referred to toluenediisocyanate, or higher-boiling solvent, and toluenediisocyanate, appropriately in a ratio of 0-40, preferably 0-10 weight percent toluenediisocyanate referred to higher boiling solvent.

For example, the following lower-boiling solvents can be considered: aromatic hydrocarbons, e.g., toluene, ethylbenzene, o-, m-, p-xylene, isopropylbenzene, chlorobenzene, o-, p- and m-dichlorobenzene, o-, m-, p-chlorotoluene, 1,2,4-trichlorobenzene. Higher-boiling solvents are, for example, diethylphthalate, diisopropylphthalate, di-n-butylphthalate, diisobutylphthalate, as well as the isophthalates and terephthalates, and furthermore, diisobutyladipate, the methyl-, ethyl-, n-butyl- and i-butylesters of n- or i-butyric acid, as well as benzophenone.

Evaporation is performed at a temperature of at least 5° C, preferably 15°-150°, and especially 30°-80° C above the boiling point of toulenediisocyanate or the solvent having a boiling point higher than toluenediisocyanate, at atmospheric pressure, elevated pressure or reduced pressure or with an inert gas feed, in a continuous or batch process. For example, the boiling points are 252° C for 2,4-toluenediisocyanate, 250° C for 2,6-toluenediisocyanate and 300° C for diethylisophthalate. Preferably, subatmospheric pressures are utilized in order to operate at lower temperatures. The starting mixture is fed from the head, appropriately through a suitable feed pipe at a feed rate of the starting mixture of 0.1-70, preferably 10-20 kg/min. Advantageously, the outlet of the feed is located 10-200 centimeters above the surface of the total mixture in the center of the evaporator. The center of the vessel and thus of the surface of the total mixture is defined as the internal circular segment which appropriately encompasses onefourth to one-half of the total surface of the mixture and thus of the total evaporator cross section.

A vessel equipped with a helical agitator is used as the evaporator. It is advisable to select a vessel with a height/diameter ratio of the total mixture of 0.5-2.5, preferably 0.7-2 to 1, with a height/inside diameter ratio of the vessel of 0.5-2.5 to 1, with a ratio of the height of the agitator in the vessel (measured as the vertical distance of the agitator inlet opening at the bottom to the level of the agitator tip) to the height of the total mixture of 0.8-1 to 1.

Preferably, cantilevered single-pitch helical agitators are used. Thus, consideration can be given to the helical agitators described in German Pat. No. 1,218,265 and surprisingly also to the conventional helical agitators, particularly those connected with an agitating shaft penetrating the vessel bottom and thus driven externally. The helix consists of compact material, e.g., cast steel, or more favorably, of a suitable hollow profile and has spiral-shaped turns with a ratio of total diameter (measured as the average distance of the outer edges of all turns) of the helical agitator to the diameter of the mixture or the inside diameter of the vessel which is advisably 0.5-0.99 to 1, and with a ratio of the width of each helix turn (profile thickness) to the diameter of the total mixture amounting to 0.1-0.5 to 1. The helix pitch, measured as the angle between helix turn and average diameter of the helical agitator, advantageously amounts to 5°-30°, particularly 6°-12°. Agitation is performed at a speed of 2-100, preferably 20-60 rpm. An agitating power of 3-30 W/kg of total mixture is suitable.

Evaporation can be performed as follows: a given concentrate is fed continuously into an evaporator under the above-mentioned conditions. As a rule, wet residues or, more favorably, those separated already in a previous evaporation, serve as a first charge. In place of the residues, other solids, for example, granular, easy-flowing insert materials in the form of beads, fragments, granules or powder, can be charged in advance in place of the residues, but for the sake of economy alone, the residue itself should be used as a solid. The concentrate is now fed with stirring with the helical agitator and a part of the residues is drawn off continuously or in portions, advantageously in an amount of 0.002-14 kg of residues per minute. By mixing with the helical agitator as described, the mixture is conducted in the center from top to bottom, then along the bottom, on the vessel wall zone from bottom to the top and then from outside to inside, while residues are suitably drawn off from the mixture at the outer top. The mixture is generally heated by heating of the vessel wall. The feed rate is suitably adjusted so that the volatile fractions of the feed have already evaporated when it is deflected at the vessel bottom. After completion of the feed, it is suitable to agitate for 0.5-60 minutes longer, to leave a suitable amount of residue in the vessel for the next evaporation and to draw off the remaining quantity of residue.

The parts cited in the following examples refer to parts by weight. The weight parts are in a ratio to volume parts as kilograms to liters.

EXAMPLE 1

A feed of 0.27 part/min. of concentrate (3 weight percent, 2,4/2,6-toluenediisocyanate, 89 weight percent diethylisophthalate, 8 weight percent residues) and a stirred tank with a cantilevered helical agitator driven from the bottom are used. The outlet of the feed is located 20 centimeters vertically above the center of the surface of a precharged mixture of dry residues (40 parts) from the 2,4/2,6-tolueneisocyanate production of a previous part of the process. The stirred tank has a ratio of height to diameter of the mixture of 1.23:1. The ratio of agitator height to mixture height amounts to 0.91:1. The helical agitator has 3 turns and is of conventional design (V2A material). The total diameter of the helical agitator has a ratio to that of the mixture in the vessel of 0.89:1, and the helical agitator width is 0.14:1. The helix pitch is 8.9° and the agitator speed is 60 rpm.

A total of 160 parts of concentrate is fed in and evaporation is performed at 250° C and 10 millimeters of mercury absolute pressure under the above-cited agitating conditions, during which 0.022 part/min. of dry residue is drawn off. Subsequently, the mixture is stirred for 30 minutes longer without a feed. A dry residue remains in the vessel. The product is recovered and the other separated volatiles are again fed to the reaction of 2,4/2,6-toluenediamine with phosgene.

The yield is 4.8 parts of 2,4/2,6-toluenediisocyanate (practically quantitative) and 142 parts of solvent (practically quantitative).

If evaporation is performed in a conventional residue pot, 3.2 parts of 2,4/2,6-toluenediisocyanate (66.7% of theory) and 135 parts of solvent (95% of theory) are obtained.

EXAMPLE 2

A feed of 0.27 part/min. of concentrate (82 weight percent of 2,4/2,6-toluenediisocyanate, 0.01 weight percent o-dichlorobenzene, 18 weight percent residues) and a stirred tank with a cantilevered bottom-driven helical agitator are used. The outlet of the feed is located 20 centimeters vertically above the center of the surface of a precharged mixture of dry residues (40 parts) from the 2,4/2,6-tolueneisocyanate production of an earlier process stage. The stirred tank has a ratio of height to diameter of the mixture of 1.23:1. The ratio of agitator height to mixture height amounts to 0.91:1. The helical agitator has 3 turns and is of conventional design (V2A material). The total diameter of the helical agitator has a ratio to that of the mixture in the vessel of 0.89:1, and the width of the helical agitator is as 0.14 to 1. The helix pitch is 8.9° and the agitator speed 60 rpm.

A total of 200 parts of concentrate are fed in and evaporation is performed at 250° C and 10 millimeters of mercury absolute pressure under the cited agitating conditions, while 0.049 part/min. of dry residue is drawn off. Then the mixture is stirred for 30 minutes longer without a feed. A dry residue remains in the vessel. The product is recovered and the other separated volatiles are recycled to the reaction of 2,4/2,6-toluenediamine with phosgene.

The yield is 164 parts of 2,4/2,6-toluenediisocyanate (practical quantitative).

If the evaporation is performed in a conventional residue pot, 145 parts of 2,4/2,6-toluenediisocyanate (88.4% of theory) are obtained.

While only the preferred embodiment of the invention is shown and described, it is intended to cover as well any change or modification therein which may be made without departing from the spirit and scope of the appended claims.

The embodiments of the invention in which an exclusive property or privilege is claimed are defined as follows:

1. A method of separating residues from a mixture of (1) residues and (2) toluenediisocyanate and solvent, said mixture being obtained by reaction of toluenediamine with phosgene in the presence of organic solvent, comprising the steps of feeding the mixture to the central portion of an evaporator equipped with a helical agitator, said evaporator being partly filled with residue and the temperature therein being maintained at least 5° C higher than the boiling point of the higher boiling component of the class consisting of toluenediisocyanate and solvent present in the mixture at the pressure within the evaporator, agitating the mixture by rotating said helical agitator at a speed of 2–100 rpm. while the mixture is fed to said evaporator, and removing the volatile components of the mixture from the evaporator in vapor form.

2. A method of separating residues as defined in claim 1, in which the mixture is fed from the top and the helical agitator is formed to cause material flow movement centrally downwards and peripherally upwards.

3. A method of separating residues as defined in claim 2, in which residue is removed from a peripheral location near the upper surface thereof during the step of feeding the mixture to the evaporator.

4. A method of separating residues as defined in claim 3, in which a substantial amount of heated residue is maintained in the evaporator during the entire addition of said mixture.

5. A method of separating residues as defined in claim 1, in which the product is recovered and the other volatiles removed in the evaporator are recycled to the process for preparing toluenediisocyanate from whence the mixture is obtained.

6. A method of separating residues as defined in claim 1, in which the evaporator is at subatmospheric pressure during the removal of volatile components.

7. A method of separating residues as defined in claim 1, in which the mixture contains solvent having a boiling point lower than the boiling point of toluenediisocyanate.

8. A method of separating residues as defined in claim 7, in which the temperature within the evaporator is maintained between about 30° C and 80° C higher than the boiling point of toluenediisocyanate at the pressure conditions within the evaporator.

9. A method of separating residues as defined in claim 1, in which the mixture contains solvent having a boiling point higher than the boiling point of toluenediisocyanate.

10. A method of separating residues as defined in claim 9, in which the temperature within the evaporator is maintained between about 30° C and 80° C higher than the boiling point of the solvent at the pressure conditions within the evaporator.

11. A method of separating residues as defined in claim 1, in which the mixture is fed at a rate sufficiently slow that substantially all of the volatile components thereof are vaporized from the added mixture before the currents carrying the added mixture reach the walls of the evaporator.

* * * * *